United States Patent
Kudo et al.

(10) Patent No.: US 9,373,020 B2
(45) Date of Patent: Jun. 21, 2016

(54) MEASUREMENT DATA SELECTION METHOD FOR BIOMETRIC DEVICE, LIGHT EXIT POSITION DETERMINATION METHOD FOR BIOMETRIC DEVICE, AND BIOMETRIC DEVICE

(71) Applicants: University of Tsukuba, Tsukuba-shi, Ibaraki (JP); HAMAMATSU PHOTONICS K.K., Hamamatsu-shi, Shizuoka (JP)

(72) Inventors: Hiroyuki Kudo, Tsukuba (JP); Naoya Saito, Tsukuba (JP); Yukio Ueda, Hamamatsu (JP); Kenji Yoshimoto, Hamamatsu (JP); Yutaka Yamashita, Hamamatsu (JP)

(73) Assignees: UNIVERSITY OF TSUKUBA, Tsukuba-shi, Ibaraki (JP); HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 0 days.

(21) Appl. No.: 14/409,293

(22) PCT Filed: Jun. 27, 2013

(86) PCT No.: PCT/JP2013/067694
§ 371 (c)(1),
(2) Date: Dec. 18, 2014

(87) PCT Pub. No.: WO2014/003133
PCT Pub. Date: Jan. 3, 2014

(65) Prior Publication Data
US 2015/0169933 A1 Jun. 18, 2015

(30) Foreign Application Priority Data

Jun. 29, 2012 (JP) .................................. 2012-147138
Jul. 4, 2012 (JP) .................................. 2012-150793

(51) Int. Cl.
*G06K 9/00* (2006.01)
*A61B 5/00* (2006.01)
*G06T 7/00* (2006.01)
*A61B 5/05* (2006.01)
*A61B 8/00* (2006.01)

(52) U.S. Cl.
CPC ............ *G06K 9/0014* (2013.01); *A61B 5/0073* (2013.01); *G06T 7/004* (2013.01); *A61B 2576/00* (2013.01); *G06T 2207/10101* (2013.01)

(58) Field of Classification Search
CPC ............... A61B 5/00; G06K 9/00; G06T 7/00
USPC ......... 382/128, 129, 130, 131, 132, 133, 134; 378/4, 8, 21–27, 101, 901; 600/407, 600/410, 411, 425, 427
See application file for complete search history.

(56) References Cited

U.S. PATENT DOCUMENTS 7,217,266 B2 * 5/2007 Anderson ............ A61B 5/0059 606/10
7,613,502 B2 * 11/2009 Yamamoto ............. A61B 5/064 600/473

FOREIGN PATENT DOCUMENTS

WO WO-2005/110239 A1 11/2005

OTHER PUBLICATIONS

Y. Ueda et al., "Time-Resolved Optical Mammography and Its Preliminary Clinical Results," Technology in Cancer Research and Treatment, 2011, pp. 393-401, vol. 10, No. 5.

*Primary Examiner* — Abolfazl Tabatabai
(74) *Attorney, Agent, or Firm* — Drinker Biddle & Reath LLP

(57) ABSTRACT

In measurement data selection, when a vector composed of measurement data obtained for respective combinations of light emitting positions, light detection positions, and resolving times in a time-resolved waveform is given as y, a vector in which pixel values of learning image data are components is given as x, and a system matrix for calculating internal image data from the measurement data is given as $A_1$, the vector y which meets the conditional expressions (2) and (3)

$$\min\|y\|_0^0 \qquad (2),$$

$$\|x - A_1^T y\|_2^2 \le \epsilon^2 \qquad (3)$$

or the conditional expression (4)

$$\min(\|y\|_0^0 + \beta\|x - A_1^T y\|_2^2) \qquad (4)$$

is determined, and upon measurement of a subject, only the measurement data corresponding to nonzero components of the vector y is used to prepare the internal image data.

6 Claims, 19 Drawing Sheets

Fig.3
(a)
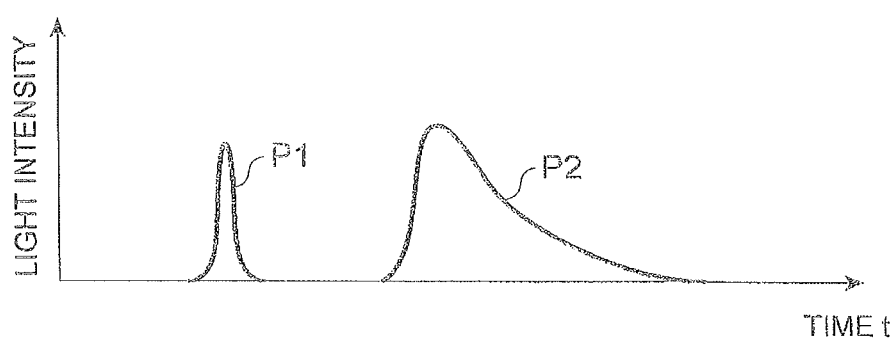
(b)
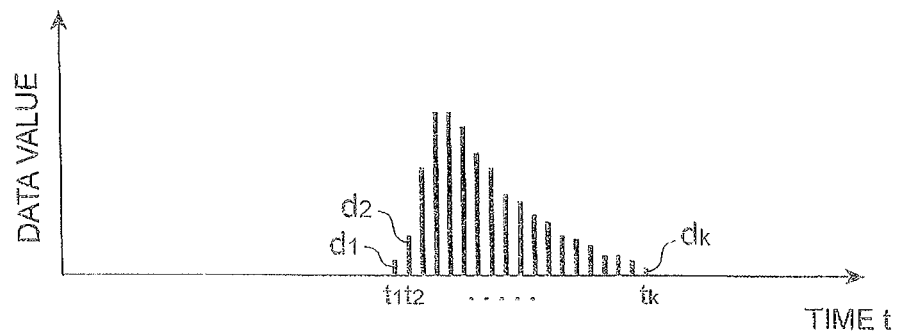

Fig. 6
(a)
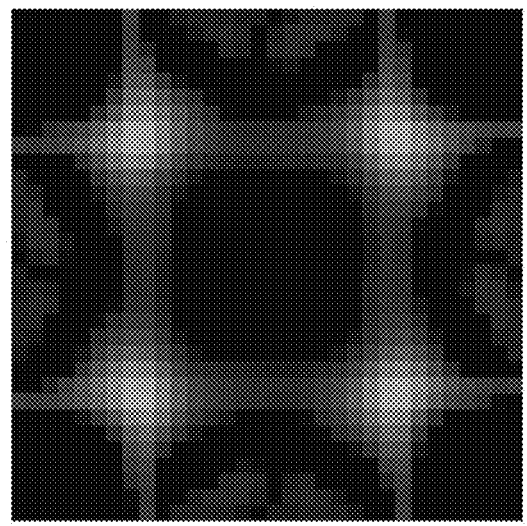
(b)
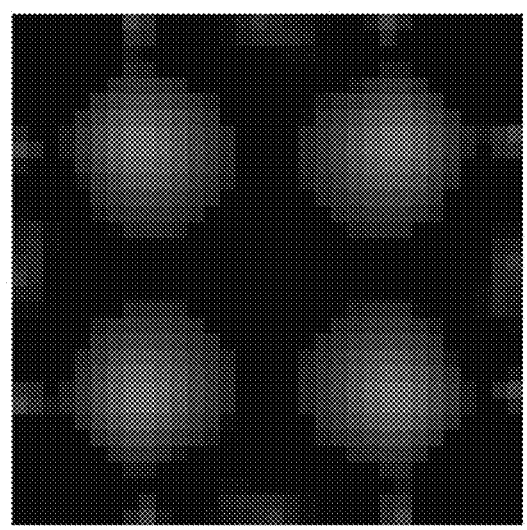

Fig. 7
(a)
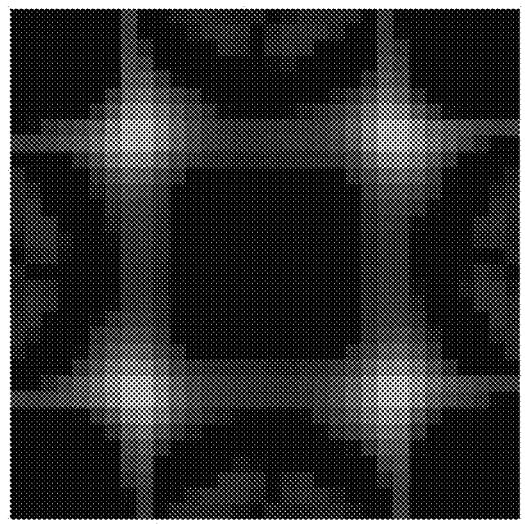
(b)
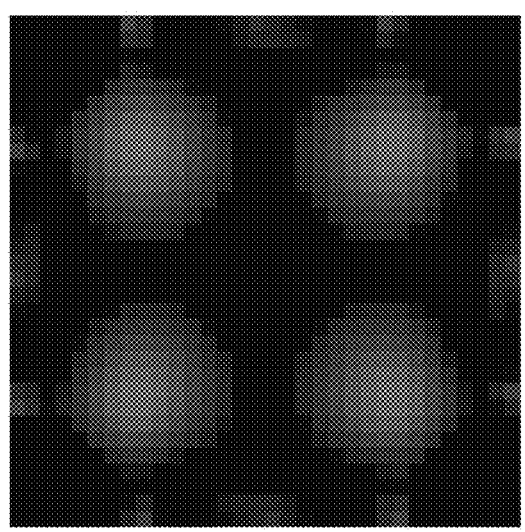

Fig. 8
(a)
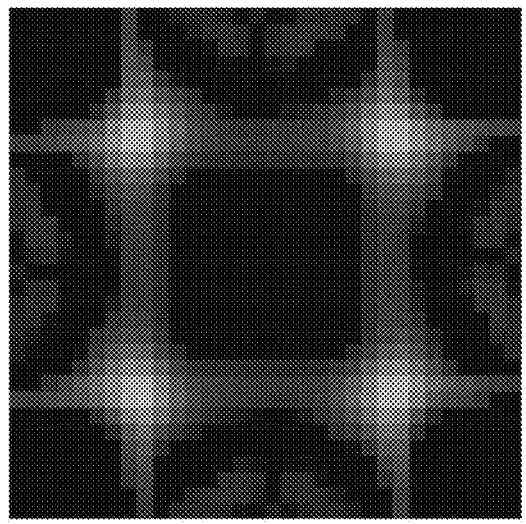
(b)
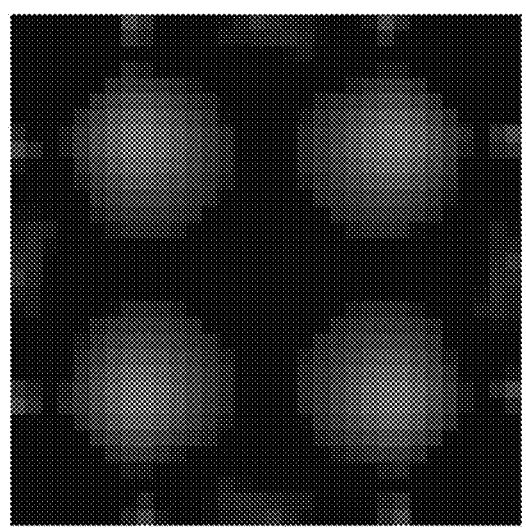

Fig. 13
(a) 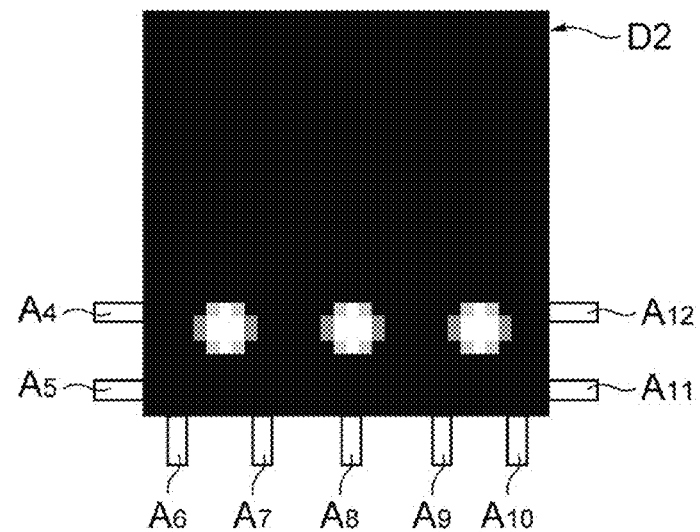
(b) 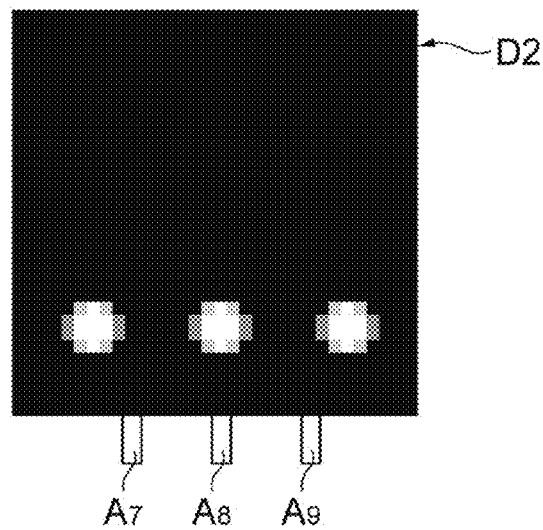
(c) 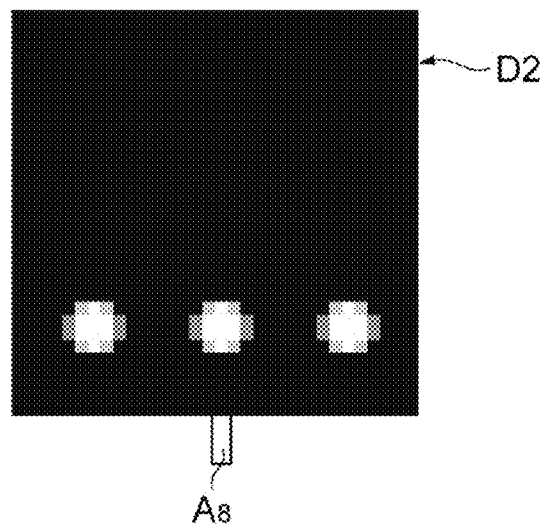

Fig. 14
(a)
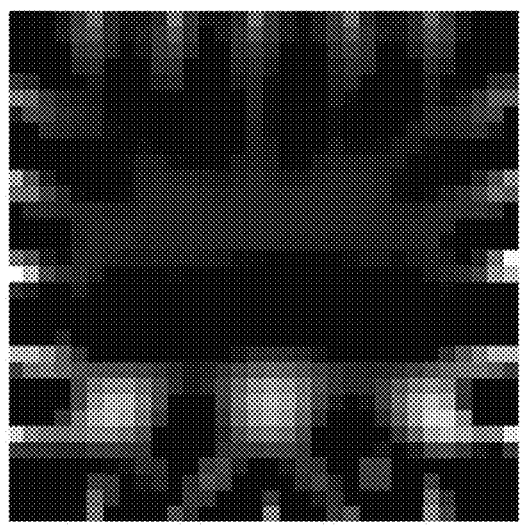
(b)
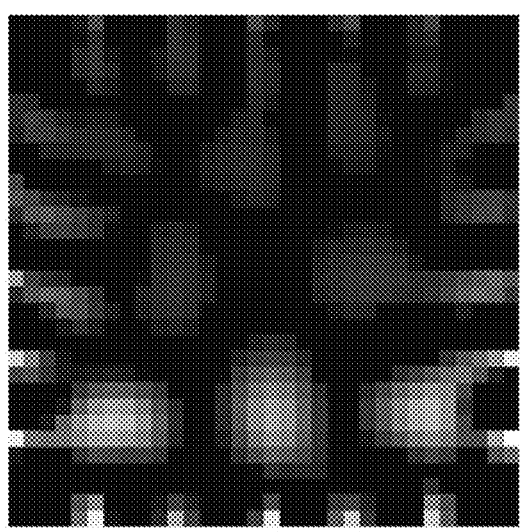

Fig. 15
(a)
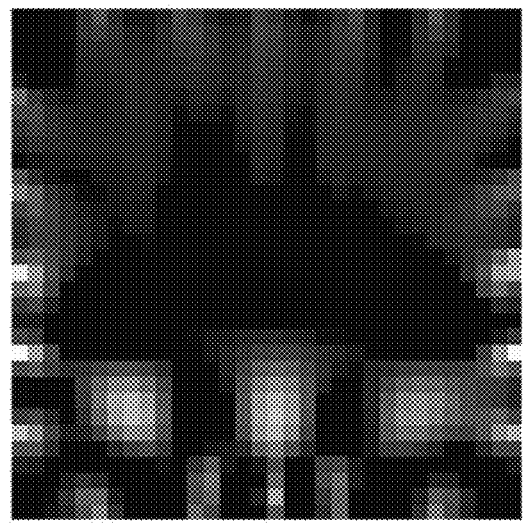
(b)
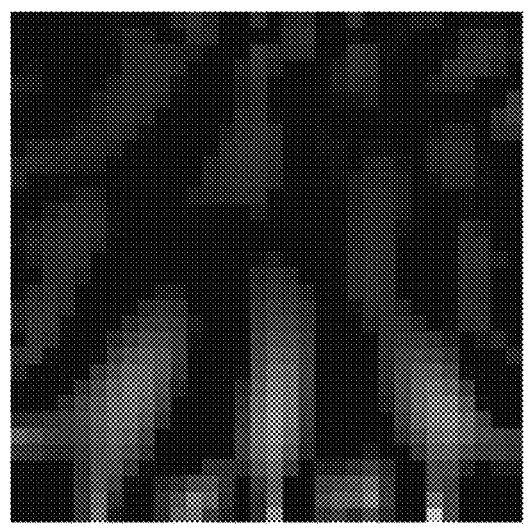

Fig. 16
(a)
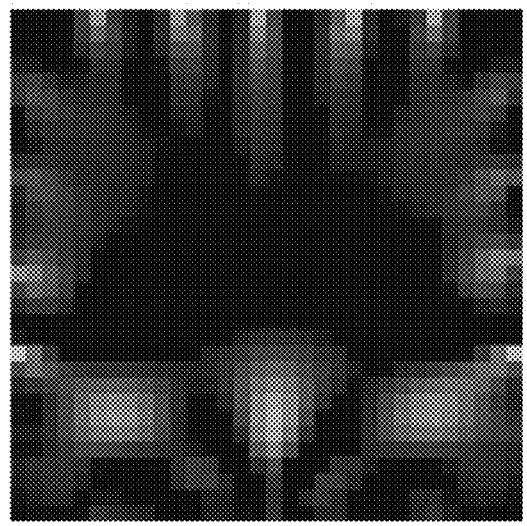
(b)
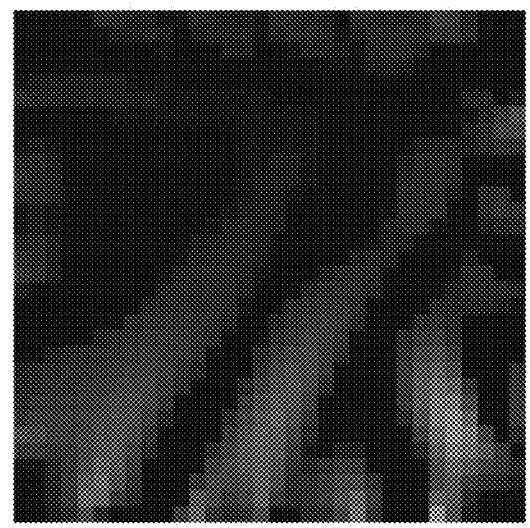

Fig.18
(a)
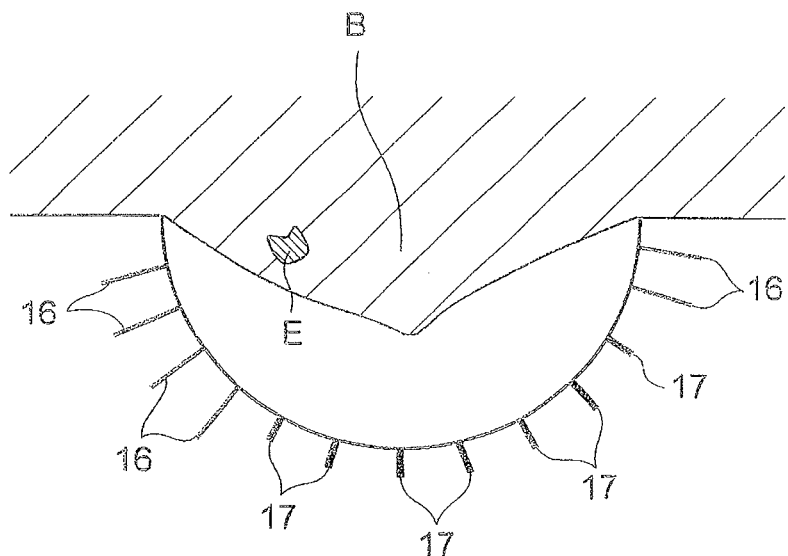
(b)
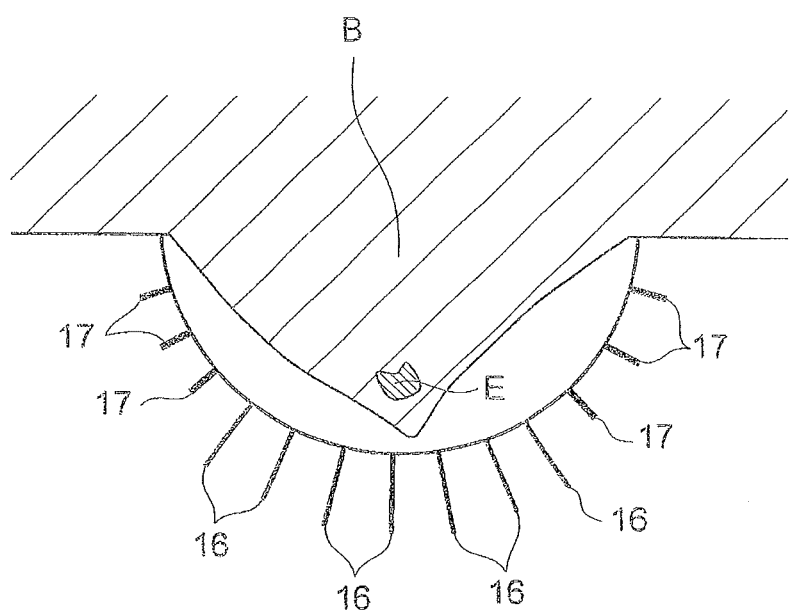

MEASUREMENT DATA SELECTION METHOD FOR BIOMETRIC DEVICE, LIGHT EXIT POSITION DETERMINATION METHOD FOR BIOMETRIC DEVICE, AND BIOMETRIC DEVICE

TECHNICAL FIELD

The present invention relates to a measurement data selection method for a bioinstrumentation apparatus, a light emitting position determination method for a bioinstrumentation apparatus, and a bioinstrumentation apparatus.

BACKGROUND ART

As an apparatus for non-invasively measuring internal information of a living body such as a head and a breast, an apparatus which makes use of light absorbing characteristics of a living body to obtain the internal information, that is, an apparatus which uses so-called diffuse optical tomography (DOT; Diffuse Optical Tomography), has been proposed. With such a measuring device, a region of a living body to be measured is irradiated with light from a predetermined irradiation position, and light which is propagated while being scattered in an inside of the region is detected at a predetermined detection position. Then, internal information on the region, that is, information on a light absorbing body such as a tumor, etc., present in the inside of the region can be obtained from measurement results of intensity, time waveform, etc. For example, Non-Patent Document 1 has described a method for conducting three-dimensional optical imaging of a living body by the use of a multi-channel time-resolved spectroscopic measurement apparatus.

CITATION LIST

Non Patent Literature

Non-Patent Document 1: Y. Ueda, K. Yoshimoto, E. Ohmae, T. Suzuki, T. Yamanaka, D. Yamashita, H. Ogura, C. Teruya, H. Nasu, E. Imi, H. Sakahara, M. Oda, Y. Yamashita, "Time-Resolved Optical Mammography and Its Preliminary Clinical Results," Technology in Cancer Research and Treatment, Vol. 10, No. 5, pp. 393-401, (2011)

SUMMARY OF INVENTION

Technical Problem

In general, calculation (image reconstruction) for preparing image data in diffuse optical tomography is formulated by a linear equation such as the expression (1) shown below. Here, a vector x is an n-dimensional vector which represents image data (n is the number of pixels). A vector y is an m-dimensional vector which represents measurement data (m is the number of data). A matrix A is a system matrix of m rows and n columns which relates the vectors x and y.

[Formula 1]

$$Ax = y \quad (1)$$

Image reconstruction in diffuse optical tomography means that the vector x is inversely calculated on the basis of the expression (1).

Here, diffuse optical tomography is characterized by being extremely large in the number of measurement data as compared with other methods such as X-ray CT and positron emission tomography (PET). In particular, in diffuse optical tomography which makes use of time-resolved spectroscopy (Time Resolved Spectroscopy; TRS), an amount of measurement data is a product of the number of light detection positions and the number of time resolving steps. In the case of two-dimensional reconstruction, one example thereof has 28800 pieces of data. The number of data which has been described above is much larger than image data (one example thereof contains 4096 pixels of 64 rows and 64 columns), which contributes to the length in time necessary for calculating the image data. In the case of three-dimensional reconstruction, data is much larger in the amount.

An object of the present invention is to provide a measurement data selection method for a bioinstrumentation apparatus, a light emitting position determination method for a bioinstrumentation apparatus, and a bioinstrumentation apparatus which is capable of reducing the number of measurement data necessary for preparing image data to shorten the time for preparing the image data.

Solution to Problem

A measurement data selection method for a bioinstrumentation apparatus according to one embodiment of the present invention is a method for selecting measurement data used for preparing internal image data in a bioinstrumentation apparatus which emits pulse-shaped light to a measurement region of a subject from a plurality of light emitting positions to prepare the internal image data of the measurement region on the basis of a time-resolved waveform of diffused light from the measurement region obtained at a plurality of light detection positions. In this method, when a vector which is composed of measurement data $y_1$ to $y_{N1}$ (where N1 is an integer of 2 or more) obtained for respective combinations of the plurality of light emitting positions, the plurality of light detection positions, and a plurality of resolving times in the time-resolved waveform is given as

[Formula 2]

$$y = \begin{pmatrix} y_1 \\ y_2 \\ \vdots \\ y_{N1} \end{pmatrix}, \quad (2)$$

a vector in which pixel values of learning image data provided in advance as an example of the internal image data are components is given as x, and a system matrix for calculating the internal image data from the measurement data $y_1$ to $y_{N1}$ is given as $A_1$, the vector y which meets the following conditional expressions (3) and (4)

[Formula 3]

$$\min \|y\|_0^0 \quad (3)$$

[Formula 4]

$$\|x - A_1^T y\|_2^2 \leq \epsilon^2 \quad (4)$$

(where $\epsilon$ is any given constant number) or which meets the following conditional expression (5)

[Formula 5]

$$\min(\|y\|_0^0 + \beta \|x - A_1^T y\|_2^2) \quad (5)$$

(where β is any given constant number) is determined by inverse calculation, and upon measurement of the subject, only measurement data corresponding to components of the vector y which are not zero is used to prepare the internal image data.

Further, a bioinstrumentation apparatus according to one embodiment of the present invention is provided with a light emitting unit emitting pulse-shaped light to a measurement region of a subject from a plurality of light emitting positions, and a computing unit preparing internal image data of the measurement region on the basis of a time-resolved waveform of diffused light from the measurement region obtained at a plurality of light detection positions. When a vector composed of measurement data $y_1$ to $y_{N1}$ (where N1 is an integer of 2 or more) obtained for respective combinations of the plurality of light emitting positions, the plurality of light detection positions, and a plurality of resolving times in the time-resolved waveform is given as

[Formula 6]

$$y = \begin{pmatrix} y_1 \\ y_2 \\ \vdots \\ y_{N1} \end{pmatrix}, \quad (6)$$

a vector in which pixel values of learning image data provided in advance as an example of the internal image data are components is given as x, and a system matrix for calculating the internal image data from the measurement data $y_1$ to $y_{N1}$ is given as $A_1$, the computing unit determines by reverse calculation the vector y which meets the following conditional expressions (7) and (8)

[Formula 7]

$$\min\|y\|_0^0 \quad (7)$$

[Formula 8]

$$\|x - A_1^T y\|_2^2 \leq \epsilon^2 \quad (8)$$

(where ε is any given constant number) or which meets the following conditional expression (9)

[Formula 9]

$$\min(\|y\|_0^0 + \beta\|x - A_1^T y\|_2^2) \quad (9)$$

(where β is any given constant number), and upon measurement of the subject, prepares the internal image data by using only measurement data corresponding to components of the vector y which are not zero.

In the above-described measurement data selection method for the bioinstrumentation apparatus and the bioinstrumentation apparatus, the vector y which meets the above-described conditional expressions (3) and (4) or the conditional expression (5) (or which meets the conditional expressions (7) and (8) or the conditional expression (9)) is determined. The conditional expressions (3) and (7) are conditions for minimizing an L0 norm of the vector y, and further, the conditional expressions (4) and (8) are constraint conditions which suppress a reconstruction error $\epsilon^2$ to a predetermined value or less upon reconstruction of the same image data as the learning image data. Still further, the conditional expressions (5) and (9) are such that the conditional expressions (3), (4) and (7), (8), which are constraint-containing problems, are rewritten into constraint-free problems.

Therefore, the vector y which meets the conditional expressions (3) and (4) or the conditional expression (5) (or which meets the conditional expressions (7) and (8) or the conditional expression (9)) is such that a reconstruction error is suppressed within a tolerance, and the number of measurement data that is not zero among the measurement data $y_1$ to $y_{N1}$ is minimized. In the above-described vector y, the measurement data which is zero is not necessary for obtaining image data in which the reconstruction error is within a tolerance, and the measurement data which is not zero is minimally necessary measurement data.

In the above-described measurement data selection method and the bioinstrumentation apparatus, upon measurement of the subject after calculation of the vector y which indicates the minimally necessary measurement data, only the minimally necessary measurement data is used to prepare internal image data. Therefore, it is possible to reduce the number of measurement data and shorten the time for preparing the image data.

Further, in the above-described measurement data selection method for the bioinstrumentation apparatus and the bioinstrumentation apparatus, calculation may be performed by replacing an L0 norm of the vector y in the conditional expressions (3) and (5) (or the conditional expressions (7) and (9)) with an L1 norm of the vector y. It is, thereby, possible to easily calculate a norm of the vector y and shorten the time for calculating the minimally necessary measurement data.

Further, in the above-described measurement data selection method for the bioinstrumentation apparatus and the bioinstrumentation apparatus, M pieces (where M is an integer of 2 or more) of the learning image data may be provided in advance, vectors in which pixel values of the M pieces of the learning image data are components may be given as $x_1$ to $x_M$, and calculation may be performed by replacing $$\|x - A_1^T y\|_2^2 \quad \text{[Formula 10]}$$

in the conditional expressions (4) and (5) (or the conditional expressions (8) and (9)) with $$\sum_{i=1}^{M} \|x_i - A_1^T y\|_2^2. \quad \text{[Formula 11]}$$

It is, thereby, possible to select the measurement data appropriate not only for specific learning image data but also for various kinds of learning image data.

Further, in the above-described measurement data selection method for the bioinstrumentation apparatus and the bioinstrumentation apparatus, when the measurement data obtained for the respective combinations of the plurality of light emitting positions, the plurality of light detection positions, and the plurality of resolving times in the time-resolved waveform are classified into N2 (where N2 is an integer of 2 or more) groups according to a predetermined rule, a vector composed of vectors $y_1$ to $y_{N2}$ in which measurement data for the respective N2 groups are components is given as

[Formula 12]

$$y = \begin{pmatrix} y_1 \\ y_2 \\ \vdots \\ y_{N2} \end{pmatrix}, \quad (12)$$

a vector in which pixel values of the learning image data provided in advance as an example of the internal image data are components is given as x, and a system matrix for calculating the internal image data from the vectors $y_1$ to $y_{N2}$ is given as $A_2$, in place of the conditional expressions (3) to (5), the vector y which meets the following conditional expressions (13) and (14)

[Formula 13]

$$\min \sum_{j=1}^{N2} \|y_j\|_2^0 \left(\|y_j\|_2^0 = \lim_{\varepsilon \to +0} \|y_j\|_2^\varepsilon\right) \quad (13)$$

[Formula 14]

$$\|x - A_2^T y\|_2^2 \leq \varepsilon^2 \quad (14)$$

(where $\epsilon$ is any given constant number) or which meets the following conditional expression (15)

[Formula 15]

$$\min \left(\sum_{j=1}^{N2} \|y_j\|_2^0 + \beta \|x - A_2^T y\|_2^2\right) \left(\|y_j\|_2^0 = \lim_{\varepsilon \to +0} \|y_j\|_2^\varepsilon\right) \quad (15)$$

(where β is any given constant number) may be determined by inverse calculation, and upon measurement of the subject, only measurement data corresponding to components of the vector y which are not zero may be used to prepare the internal image data.

In the above-described measurement data selection method for the bioinstrumentation apparatus and the bioinstrumentation apparatus, in place of the vector y in which measurement data are components, the measurement data are classified into a plurality of groups according to a predetermined rule, and the vector y composed of the vectors $y_1$ to $y_{N2}$ in which the measurement data for the respective plurality of groups are components is used to compute the above-described conditional expression. It is, thereby, possible to know a group which is not necessary for obtaining image data in which a reconstruction error is within a tolerance, among the plurality of groups classified according to the predetermined rule. Here, the measurement data are obtained for respective combinations of the plurality of light emitting positions, the plurality of light detection positions, and the plurality of resolving times in the time-resolved waveform and, therefore, typical examples of the above-described predetermined rule include classification based on the light emitting position, classification based on the light detection position, and classification based on the resolving time.

In the above-described measurement data selection method and the bioinstrumentation apparatus, upon measurement of the subject after calculation of the vector y which indicates the minimally necessary groups of the measurement data, only the minimally necessary measurement data group is used to prepare the internal image data. It is, therefore, possible to reduce the number of measurement data and shorten the time for preparing image data.

Further, in the above-described measurement data selection method for the bioinstrumentation apparatus and the bioinstrumentation apparatus, the measurement data obtained for the respective combinations of the plurality of light emitting positions, the plurality of light detection positions, and the plurality of resolving times in the time resolved waveform may be classified by the plurality of resolving times to give the vectors $y_1$ to $y_{N2}$. It is, thereby, possible to exclude measurement data obtained at a resolving time which influences the respective pixel values of the internal image data to a lesser extent, and use only measurement data obtained at a resolving time which influences the respective pixel values to a greater extent, and thus, it is possible to shorten effectively the time for preparing the internal image data.

Further, the above-described bioinstrumentation apparatus may be configured such that the computing unit classifies the measurement data obtained for the respective combinations of the plurality of light emitting positions, the plurality of light detection positions, and the plurality of resolving times in the time-resolved waveform by the plurality of light emitting positions to give the vectors $y_1$ to $y_{N2}$, and determines by inverse calculation the vector y which meets the conditional expressions (13) and (14) or the conditional expression (15), and the bioinstrumentation apparatus further comprises light emitting position changeable means which is constituted in such a manner that light emitting means for emitting the light is allowed to move to or allowed to be arranged selectively at the light emitting position corresponding to components of the vector y which are not zero. Thereby, the apparatus can be constituted so as to exclude a light emitting position which influences the respective pixel values of the internal image data to a lesser extent, and to emit light only from a light emitting position which influences the respective pixel values to a greater extent, and thus, it is possible to simplify a configuration of the apparatus by reducing the number of light emitting means and also to shorten effectively the time for preparing the internal image data.

Further, a light emitting position determination method for the bioinstrumentation apparatus according to one embodiment of the present invention is a method for determining the light emitting position by using the above-described measurement data selection method for the bioinstrumentation apparatus. In this method, the measurement data obtained for the respective combinations of the plurality of light emitting positions, the plurality of light detection positions, and the plurality of resolving times in the time-resolved waveform are classified by the plurality of light emitting positions to give the vectors $y_1$ to $y_{N2}$, and the vector y which meets the conditional expressions (13) and (14) or the conditional expression (15) is determined by inverse calculation. Then, upon measurement of the subject or upon manufacture of the bioinstrumentation apparatus, light emitting means for emitting the light is arranged only at the light emitting position corresponding to components of the vector y which are not zero. Thereby, it is possible to exclude measurement data corresponding to a light emitting position which influences the respective pixel values of the internal image data to a lesser extent, and use only measurement data corresponding to a light emitting position which influences the respective pixel values to a greater extent, and thus, it is possible to shorten effectively the time for preparing the internal image data.

Advantageous Effects of Invention

In accordance with the measurement data selection method for the bioinstrumentation apparatus, the light emitting position determination method for the bioinstrumentation apparatus, and the bioinstrumentation apparatus according to one embodiment of the present invention, it is possible to reduce the number of measurement data necessary for preparing image data and shorten the time for preparing the image data.

BRIEF DESCRIPTION OF DRAWINGS

FIG. 3 (a) in FIG. 3 is a drawing which schematically shows, as an example, a waveform of measurement light emitted from a certain light emitting position and a waveform of scattered light detected at a certain light detection position after propagation through the inside of the measurement region. (b) in FIG. 3 is a drawing which shows data values for the respective times when the scattered light shown in (a) is detected for the intensity and subjected to time resolution.

FIG. 6 (a) in FIG. 6 is a drawing which shows internal image data when reconstruction is carried out by using only measurement data obtained at 23 selected resolving times. (b) in FIG. 6 is a drawing which shows internal image data, as a comparative example, when 23 resolving times are selected at random.

FIG. 7 (a) in FIG. 7 is a drawing which shows internal image data when reconstruction is carried out by using only measurement data obtained at 17 selected resolving times. (b) in FIG. 7 is a drawing which shows internal image data, as a comparative example, when 17 resolving times are selected at random.

FIG. 8 (a) in FIG. 8 is a drawing which shows internal image data when reconstruction is carried out by using only measurement data obtained at 11 selected resolving times. (b) in FIG. 8 is a drawing which shows internal image data, as a comparative example, when 11 resolving times are selected at random.

FIG. 13 includes drawings which show light emitting positions selected in the second example.

FIG. 14 (a) in FIG. 14 is a drawing which shows internal image data when only measurement data corresponding to 9 selected light emitting positions are used to carry out reconstruction. (b) in FIG. 14 is a drawing which shows internal image data, as a comparative example, when 9 light emitting positions are selected at random.

FIG. 15 (a) in FIG. 15 is a drawing which shows internal image data when only measurement data corresponding to 3 selected light emitting positions are used to carry out reconstruction. (b) in FIG. 15 is a drawing which shows internal image data, as a comparative example, when 3 light emitting positions are selected at random.

FIG. 16 (a) in FIG. 16 is a drawing which shows internal image data when only measurement data corresponding to 1 selected light emitting position is used to carry out reconstruction. (b) in FIG. 16 is a drawing which shows internal image data, as a comparative example, when 1 light emitting position is selected at random.

FIG. 18 includes drawings which show examples in which light emitting/measurement ends are disposed depending on a site at which a tumor is present where the tumor to be measured is present inside a measurement region.

DESCRIPTION OF EMBODIMENTS

Hereinafter, a description will be given in detail of embodiments of the measurement data selection method for the bioinstrumentation apparatus, the light emitting position determination method for the bioinstrumentation apparatus, and the bioinstrumentation apparatus with reference to the accompanying drawings. In addition, in the description of the drawings, elements identical to each other are provided with the same reference symbols, and overlapping description will be omitted.

First Embodiment

Figure 1:
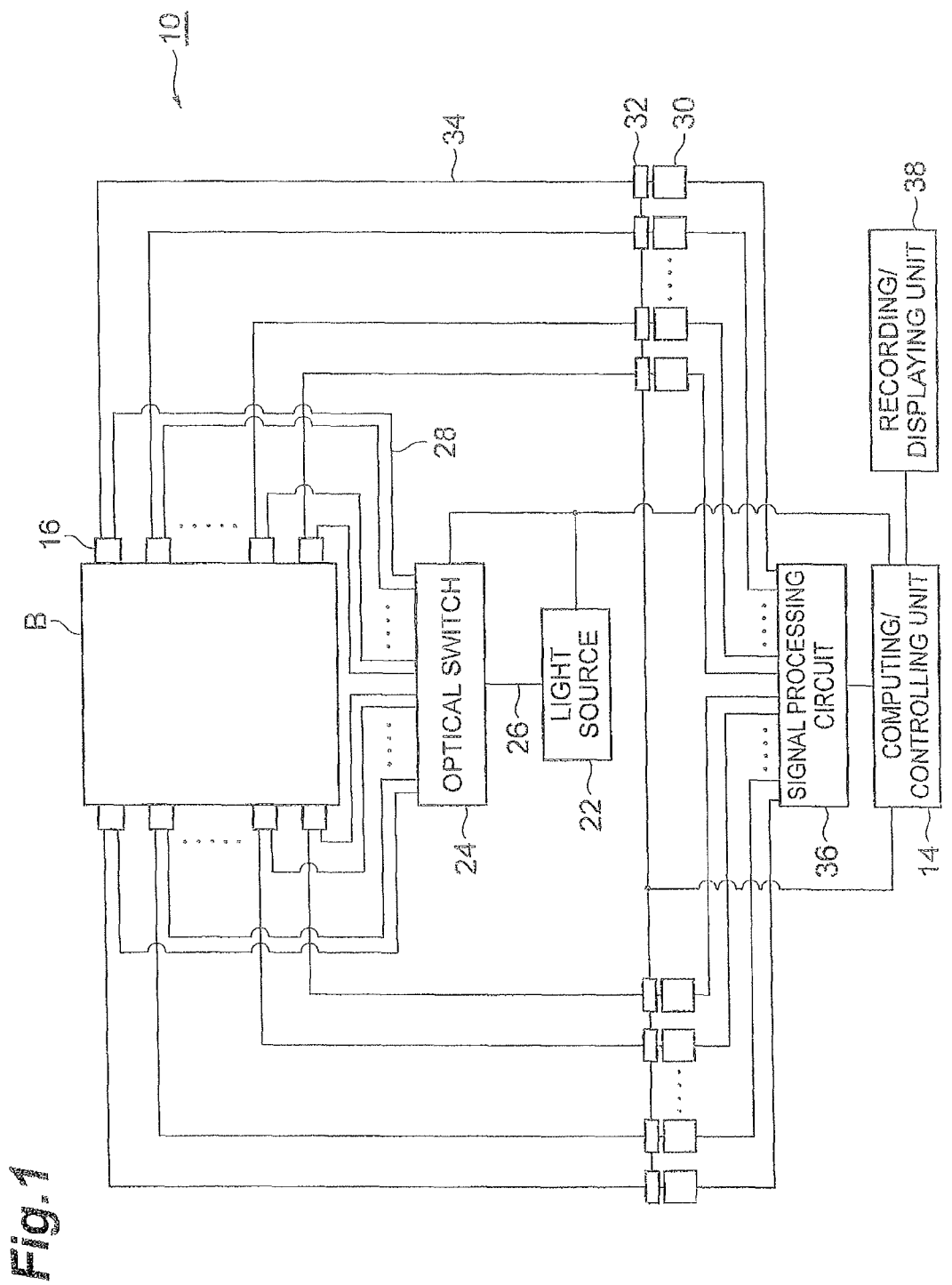
FIG. 1 is a drawing which shows a configuration of a bioinstrumentation apparatus according to a first embodiment of the present invention.

FIG. 1 is a drawing which shows a configuration of a bioinstrumentation apparatus 10 according to a first embodiment. The bioinstrumentation apparatus 10 of the present embodiment is a so-called TRS-based diffuse optical tomography apparatus, and the apparatus irradiates a measurement region B of a subject, that is, a measurement object, with light, detects diffused light (returned light), and estimates an average flight path of photons and an average optical path length on the basis of a detection position thereof and data on measured light intensity (for example, a time-resolved histogram of photons), thereby imaging information on an inside of the body as an image reconstructing problem. An image obtained by this device is visualization of, for example, a position of a tumor, a distribution of oxygenated hemoglobin and deoxygenated hemoglobin, that is, a functional image of tissues of the body. In addition, for example, a head and a female breast, etc., are assumed to be the measurement region B.

The bioinstrumentation apparatus 10 is provided with a light irradiation unit which irradiates the inside of the measurement region B with measurement light, a light detection unit which detects diffused light occurring from the measurement region B by irradiation of light from the light irradiation unit, and a computing unit 14 which calculates a spatial distribution of absorption coefficients of the measurement region B on the basis of an output signal from the light detection unit, thereby generating a reconstructed image of the measurement region B.

The light irradiation unit is a part for emitting light to the measurement region B of the subject from a plurality of light emitting positions. The light irradiation unit of the present embodiment is constituted with light emitting ends (light emitting means) included respectively in n light emitting/measurement ends 16 (n is an integer of 2 or more) installed on the measurement region B, a light source 22, and an optical switch 24. As the light source 22, for example, a laser diode can be used. A wavelength of the measurement light is preferably a wavelength of a near infrared region which is approximately from 700 nm to 900 nm in view of a relationship between transmittance of a living body and an absorption coefficient of an absorbing body to be quantified or others.

The measurement light is emitted from the light source 22, for example, as continuous light. The measurement light emitted from the light source 22 is irradiated from the light emitting/measurement ends 16 to the measurement region B. The optical switch 24 is an optical switch which outputs n for one input, inputs light from the light source 22 via a light source optical fiber 26, and successively provides the light to each of the n light emitting/measurement ends 16. That is, the optical switch 24 selects successively one by one the n emission optical fibers 28 connected respectively to the light emitting/measurement ends 16, and optically connects the emission optical fiber 28 with the light source 22.

The light detection unit is a part for detecting the intensity of diffused light from the measurement region B at a plurality of light detection positions. The light detection unit of the present embodiment is constituted with light measurement ends included respectively in the above-described n light emitting/measurement ends 16, n photodetectors 30 corresponding respectively to the n light emitting/measurement ends 16, and n shutters 32 arranged at an input part front stage on each of the photodetectors. Diffused light emitted to the light measurement end of each of the light emitting/measurement ends 16 from the measurement region B is input into each of the n photodetectors 30 via a detection optical fiber 34. The photodetector 30 generates an analog signal according to the light intensity of diffused light which has arrived at the corresponding light emitting/measurement end 16. As the photodetector 30, various elements can be used such as a photodiode, an avalanche photodiode, and a PIN photodiode, etc., in addition to a photomultiplier tube (PMT: Photomultiplier Tube). In a case where the diffused light from the measurement region B is weak, a photodetector of high sensitivity or high gain is preferably used.

A signal processing circuit 36 is connected to a signal output end of the photodetector 30, and the signal processing circuit 36 digitizes the analog signal output from the photodetector 30 and generates measurement data which acts as a base of TRS calculation by means of time resolution. The signal processing circuit 36 provides the thus generated measurement data to the computing unit 14.

The computing unit 14 computes a light absorption coefficient distribution inside the measurement region B on the basis of the measurement data supplied from the signal processing circuit 36 to generate a reconstructed image (hereinafter, referred to as internal image data) for the inside of the measurement region B. The computing unit 14 is realized, for example, by a computer having computing means such as a CPU (Central Processing Unit) and storage means such as a memory. It is preferable that the computing unit 14 additionally has functions of controlling light emission of the light source 22, operation of the optical switch 24 and opening/closing of the shutter 32. Further, the computing unit 14 is connected to a recording/displaying unit 38, thereby enabling visualization of computation results by the computing unit 14, that is, internal image data of the measurement region B.

Calculation of the internal information on the measurement region B, that is, the internal information measurement is performed, for example, as follows. The measurement light is successively emitted to the inside of the measurement region B from each of the n light emitting/measurement ends 16 to detect the light intensity diffused through the measurement region B by the n photodetectors 30 via the n light emitting/measurement ends 16. A spatial distribution of absorption coefficients inside the measurement region B is computed on the basis of the detection results, thereby generating internal image data which includes information (internal information) on a position and shape of an absorbing body such as a tumor.

A known method which has been described in detail, for example, in Non-Patent Document 1 may be preferably used in calculating a distribution of absorption coefficients in the computing unit 14.

Here, the computing unit 14 of the present embodiment has functions to exclude measurement data which influences each pixel value of internal image data to a lesser extent and selectively use only measurement data which influences each pixel value of the internal image data to a greater extent, among a plurality of measurement data obtained from the light detection unit. Hereinafter, a description will be given of a method for selecting the measurement data by the computing unit 14. In addition, the method for selecting the measurement data described as follows may be performed upon manufacturing the bioinstrumentation apparatus 10. In this case, it is acceptable that the computing unit 14 is programmed in advance at the time of manufacture thereof so that only the thus selected measurement data is used to prepare internal image data, when the measurement region B is measured.

Figure 2:
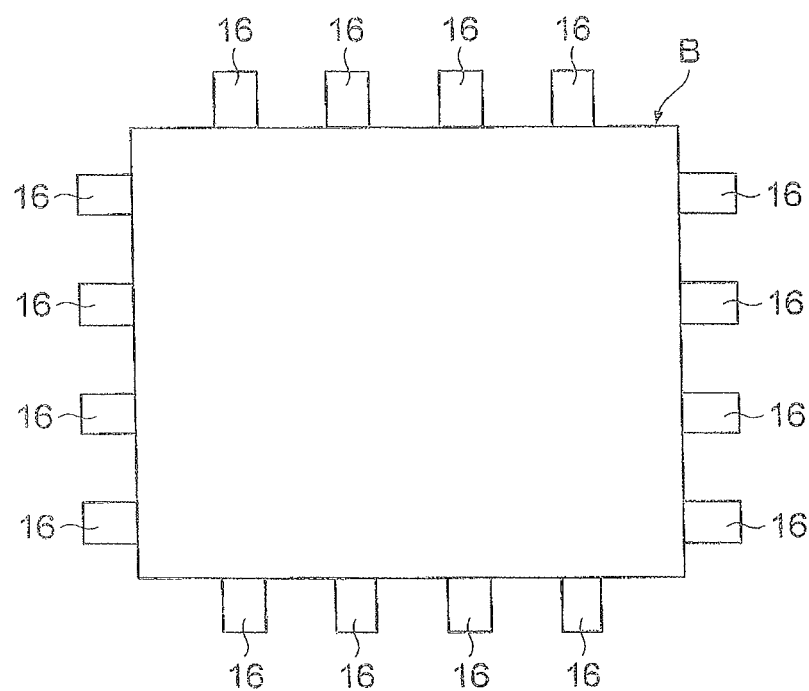
FIG. 2 is a drawing which schematically shows a measurement region and a plurality of light emitting/measurement ends.

FIG. 2 is a drawing which schematically shows the measurement region B and the plurality of light emitting/measurement ends 16. As shown in FIG. 2, the light emitting/measurement ends 16 are assumed to be arranged at m light emitting positions (where m is an integer of 2 or more, and m=16 in FIG. 2) around the measurement region B. First, the measurement light is emitted to the measurement region B from each of the m light emitting/measurement ends 16, and scattered light is measured at each of the light emitting/measurement ends 16 to obtain a plurality of measurement data. Here, the plurality of measurement data are measurement data at each time which has been subjected to time resolution at each of the light detection positions.

(a) in FIG. 3 is a drawing which schematically shows, as an example, a waveform of measurement light P1 emitted from a certain light emitting position, and a waveform of scattered light P2 detected at a certain light detection position after propagation through the inside of the measurement region B. Further, (b) in FIG. 3 is a drawing which shows data values for the respective times when the intensity of the scattered light P2 shown in (a) in FIG. 3 is detected and subjected to time resolution. In (a) in FIG. 3 and (b) in FIG. 3, the horizontal axis indicates time. In (a) in FIG. 3, the vertical axis indicates light intensity, and in (b) in FIG. 3, the vertical axis indicates a magnitude of the data value.

As shown in (a) in FIG. 3, the measurement light P1 is emitted to the measurement region B as pulse-shaped light, and the light is diffused inside the measurement region B and passes through optical paths different in length, and therefore, the waveform of the scattered light P2 becomes a shape which extends before and after in terms of time. Where the waveform of the scattered light P2 is subjected to time resolution with k sections (where k is an integer of 2 or more (the number of time resolving steps)), as shown in (b) in FIG. 3, measurement data $d_1, d_2, \ldots, d_k$ at the respective times $t_1, t_2, \ldots, t_k$ are obtained. The above-described measurement data $d_1, d_2, \ldots, d_k$ are individually obtained for each of the m light emitting positions at each of the m light measurement positions. That is, the measurement data is obtained for respective combinations of the m light emitting positions, the m light detection positions, and the k resolving times, and thus, a total of (m×m×k) measurement data are obtained.

Here, these (k×m×m) measurement data are given as measurement data $y_1$ to $y_{N1}$ (where N1 is an integer of 2 or more, N1=k×m×m). Then, the following vector y which is composed of the N1 measurement data $y_1$ to $y_{N1}$ is defined.

[Formula 16]

$$y = \begin{pmatrix} y_1 \\ y_2 \\ \vdots \\ y_{N1} \end{pmatrix} \quad (16)$$

Further, a vector in which a plurality of pixel values of internal image data are components is given as x, and a system matrix for calculating the vector x from the vector y is given as $A_1$ (refer to the previously described expression (1)).

Further, in the present embodiment, learning image data is provided in advance. The learning image data is prepared in advance as an example of the internal image data, and, for example, the data is image data that a light absorbing body is present inside a region which requires a relatively clear image quality in the internal image data prepared in the computing unit 14, for example, a region at which a tumor is likely to develop in the measurement region B. Then, the vector in which a plurality of pixel values of the learning image data are components is applied to the above-described vector x.

Then, the computing unit 14 determines the vector y which meets the following conditional expressions (17) and (18). In this case, $\epsilon$ is any given constant number.

[Formula 17]

$$\min \|y\|_0^0, \|y\|_0^0 = \lim_{\varepsilon \to +0} \sum_{i=1}^{N1} |y_i|^\varepsilon \quad (17)$$

[Formula 18]

$$\|x - A_1^T y\|_2^2 \le \varepsilon^2 \quad (18)$$

The conditional expression (17) is a condition for minimizing an L0 norm of the vector y composed of the measurement data $y_1$ to $y_{N1}$ which is an objective function of the present embodiment, and also a condition for minimizing the number of measurement data which are not zero among the measurement data $y_1$ to $y_{N1}$ used in the image reconstruction. Further, the conditional expression (18) is a constraint for suppressing a reconstruction error $\epsilon^2$ to a predetermined value or less upon reconstruction of the same image data as the learning image data. That is, the above-described conditional expressions (17) and (18) are solved, thus making it possible to decide minimally necessary measurement data which is the smallest data set in the vector y which is able to suppress a reconstruction error of the learning image data to a certain value $\epsilon^2$ or lower, when typical learning image data is provided.

Further, it is acceptable that the computing unit 14 determines the vector y which meets the following conditional expression (19) in place of the above-described conditional expressions (17) and (18). In this case, β is any given constant number.

[Formula 19]

$$\min(\|y\|_0^0 + \beta \|x - A_1^T y\|_2^2) \quad (19)$$

The conditional expression (19) is such that the conditional expressions (17) and (18), which are a constraint-containing minimization problem, are rewritten into a constraint-free minimization problem, and can be computed more easily than the conditional expressions (17) and (18). The constraint-free minimization problem can be easily solved, for example, by an iterative method which is called an iterative soft-thresholding method in a field of compressed sensing. In addition, in the conditional expressions (17) and (18), an upper limit of the reconstruction error is defined by $\epsilon$, while in the conditional expression (19), an upper limit of the reconstruction error is defined by β.

The vector y which meets the conditional expressions (17) and (18) or the conditional expression (19) is such that while a reconstruction error is suppressed within a tolerance, the number of measurement data which are not zero among the measurement data $y_1$ to $y_{N1}$ is minimized. In the above-described vector y, the measurement data which is zero is not necessary for obtaining image data in which the reconstruction error is within a tolerance, and the measurement data which is not zero is minimally necessary measurement data for obtaining the image data in which the reconstruction error is within a tolerance.

After the above-described computation, the computing unit 14 uses only measurement data of a light emitting position, a light detection position, and a resolving time which corresponds to the measurement data of not being zero among the measurement data $y_1$ to $y_{N1}$ in measurement of the measurement region B to prepare the internal image data.

In the light emitting position determination method and the bioinstrumentation apparatus 10 of the present embodiment, as described above, the vector y which shows the minimally necessary measurement data is calculated and, upon measurement of the subject, only the minimally necessary measurement data is used to prepare the internal image data. Therefore, it is possible to reduce the number of measurement data and shorten the time for preparing image data.

First Modified Example

In the above-described embodiment, the L0 norm of the vector y is minimized in the conditional expression (17), and the expression which includes the L0 norm of the vector y is also minimized in the conditional expression (19). However, since the L0 norm is a non-convex function, an amount of calculation for minimization is increased. Therefore, in the present modified example, the L0 norm of the vector y in the conditional expressions (17) and (19) is replaced with an L1 norm which is a convex function, thereby performing approximately minimization calculation. That is, the computing unit 14 may preferably determine the vector y which meets the following conditional expressions (20) and (21) or determine the vector y which meets the conditional expression (22).

[Formula 20]

$$\min \|y\|_1^1 \quad (20)$$

[Formula 21]

$$\|x - A_1^T y\|_2^2 \le \epsilon^2 \quad (21)$$

[Formula 22]

$$\min(\|y\|_1^1 + \beta \|x - A_1^T y\|_2^2) \quad (22)$$

According to the present modified example, it is possible to easily calculate a norm of the vector y, and shorten the time necessary for selecting minimally necessary measurement data.

Second Modified Example

In the above-described embodiment, one learning image data is provided in advance to calculate the conditional expressions (18) and (19). In this case, a light emitting position, a light detection position and a resolving time of the finally selected measurement data are the light emitting position, the light detection position and the resolving time which are optimal for the learning image data, and thus, image data which is different from the learning image data is not always sufficiently small in reconstruction error.

Therefore, in the present modified example, in order that various kinds of image data are decreased in reconstruction error, the number of learning image data which are to be provided in advance is two or more. That is, M pieces (M is an integer of 2 or more) of typical learning image data assumed in the measurement region B are provided in advance, and vectors in which pixel values of the M pieces of learning image data are components are given as $x_1$ to $x_M$ to perform calculation by replacing

[Formula 23]

$$\|x - A_1^T y\|_2^2 \quad (23)$$

with

[Formula 24]

$$\sum_{i=1}^{M} \|x_i - A_1^T y\|_2^2 \quad (24)$$

in the respective conditional expressions. It is, thereby, possible to select measurement data which is appropriate not only for specific learning image data but also for various kinds of learning image data and decrease a reconstruction error.

Third Modified Example

In the present modified example, (m×m×k) measurement data obtained for respective combinations of m light emitting positions, m light detection positions, and k resolving times in the above-described embodiment are classified into N2 (where N2 is an integer of 2 or more) groups according to a predetermined rule. Then, vectors $y_1$ to $y_{N2}$ in which measurement data for the respective N2 groups are components are defined, and the following vector y composed of the vectors $y_1$ to $y_{N2}$ is defined.

[Formula 25]

$$y = \begin{pmatrix} y_1 \\ y_2 \\ \vdots \\ y_{N2} \end{pmatrix} \quad (25)$$

Further, a vector in which a plurality of pixel values of internal image data are components is given as x, and a system matrix for calculating the vector x from the vector y is given as $A_2$.

Further, in the present modified example as well, learning image data similar to that used in the above-described embodiment is provided in advance. Then, a vector in which a plurality of pixel values of the learning image data are components is applied to the above-described vector x.

Then, the computing unit 14 determines the vector y which meets the following conditional expressions (26) and (27) in place of the conditional expressions (17) and (18) of the above-described embodiment.

[Formula 26]

$$\min \sum_{j=1}^{N2} \|y_j\|_2^0 \left( \|y_j\|_2^0 = \lim_{\varepsilon \to +0} \|y_j\|_2^\varepsilon \right) \quad (26)$$

[Formula 27]

$$\|x - A_2^T y\|_2^2 \leq \varepsilon^2 \quad (27)$$

The conditional expression (26) is a condition for minimizing an L0 norm of the vector y composed of vectors $y_1$ to $y_{N1}$, which is an objective function of the present embodiment, and also a condition for minimizing the number of vectors which are not zero vectors, among the vectors $y_1$ to $y_{N1}$ used in image reconstruction. Further, the conditional expression (27) is a constraint for suppressing a reconstruction error $\varepsilon^2$ to a predetermined value or less upon reconstruction of the same image data as the learning image data. That is, the above-described conditional expressions (26) and (27) are solved, by which it is possible to decide a minimum data set in the vector y capable of suppressing a reconstruction error of the learning image data to a certain value $\varepsilon^2$ or less, when typical learning image data is provided.

Further, it is also acceptable that the computing unit 14 determines the vector y which meets the following conditional expression (28) in place of the above-described conditional expressions (26) and (27).

[Formula 28]

$$\min \left( \sum_{j=1}^{N2} \|y_j\|_2^0 + \beta \|x - A_2^T y\|_2^2 \right) \left( \|y_j\|_2^0 = \lim_{\varepsilon \to +0} \|y_j\|_2^\varepsilon \right) \quad (28)$$

The conditional expression (28) is such that the conditional expressions (26) and (27), which are a constraint-containing minimization problem, are rewritten into a constraint-free minimization problem, and can be computed more easily than the conditional expressions (26) and (27).

In the present modified example, in place of the vector y of the above-described embodiment in which measurement data are components, the measurement data are classified into a plurality of groups according to a predetermined rule to compute the above-described conditional expression by using the vector y composed of the vectors $y_1$ to $y_{N2}$ in which the measurement data for the respective plurality of groups are components. Thereby, it is possible to know a group not necessary for obtaining internal image data in which a reconstruction error is within a tolerance, among the plurality of groups classified according to the predetermined rule.

Here, the measurement data are obtained for respective combinations of the m light emitting positions, the m light detection positions, and the k resolving times, and therefore, typical examples of the predetermined rule include classification according to the light emitting position, classification according to the light detection position, and classification according to the resolving time. Where the data are classified according to the light emitting position or the light detection position, N2=m. Further, where the data are classified according to the resolving time, N2=k.

In the present modified example, as described above, the vector y which shows groups of the minimally necessary measurement data is calculated and, upon measurement of the subject, only the groups of the minimally necessary measurement data (for example, only the measurement data corresponding to minimally necessary light emitting positions or only the measurement data obtained at minimally necessary resolving times) are used to prepare the internal image data. Therefore, it is possible to reduce the number of measurement data and shorten the time for preparing image data.

First Example

Figure 4:
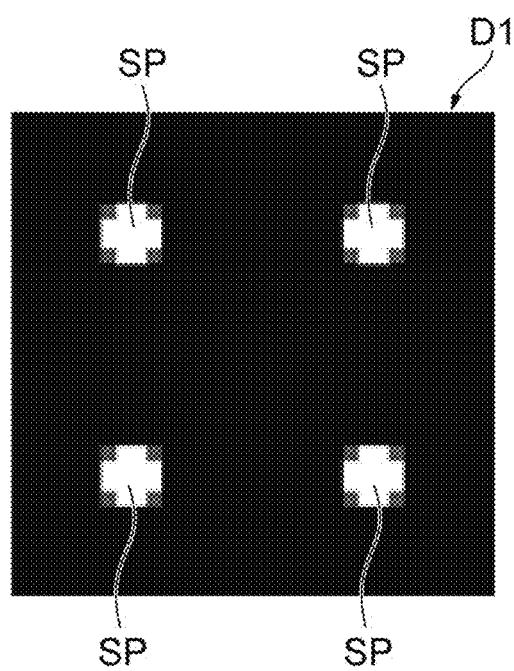
FIG. 4 is a drawing which shows learning image data used in a first example.

A description will be given of an example of a case where classification is made according to a resolving time in the above-described third modified example. FIG. 4 is a drawing which shows learning image data D1 used in the present example, and this data includes a plurality of spots SP representing a tumor or the like. Further, in the present example, the measurement condition was set as follows,
Image size: 32×32
The number of light emitting positions: 12
The number of light detection positions: 12
Measurement time: 20 nano seconds
The number of resolving times (the number of time samplings): k=140
Total number of measurement data: 20160

Then, the measurement was carried out under the above-described conditions to obtain 20160 pieces of measurement data. The thus obtained measurement data were classified by the resolving times to give vectors $y_1$ to $y_{140}$ thereby defining the following vector y composed of the vectors $y_1$ to $y_{140}$.

[Formula 29]

$$y = \begin{pmatrix} y_1 \\ y_2 \\ \vdots \\ y_{140} \end{pmatrix} \quad (29)$$

Figure 5:
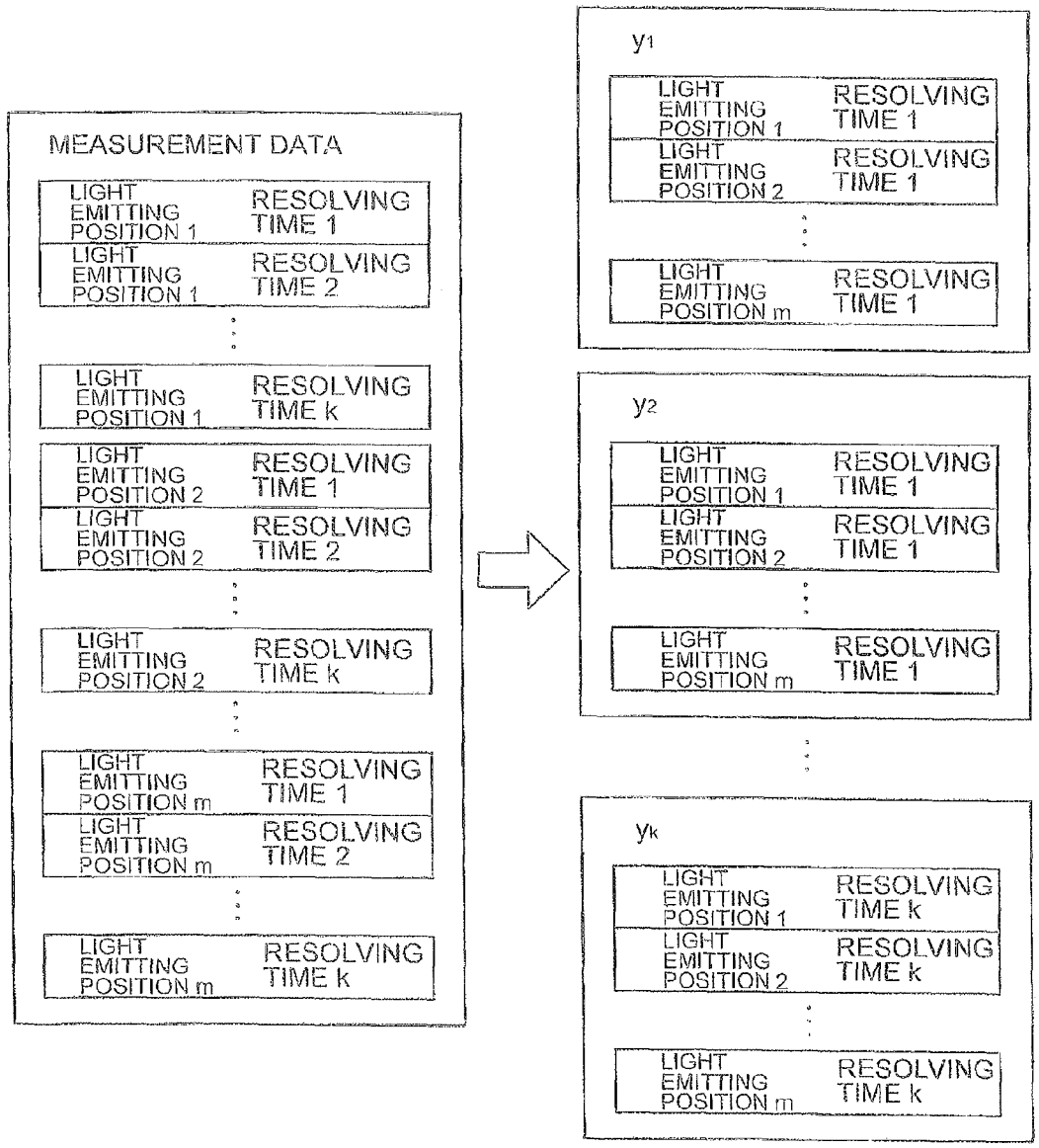
FIG. 5 is a drawing which conceptually shows an operation in which a plurality of measurement data are classified by the resolving times to give vectors $y_1$ to $y_k$.

In addition, FIG. 5 is a drawing which conceptually shows an operation in which a plurality of measurement data are classified by the resolving times to give vectors $y_1$ to $y_k$.

Then, under the condition that a reconstruction error is $\beta=1.25$, a vector y which met the conditional expression (28) was determined, and a vector which was not a zero vector among component vectors $y_1$ to $y_{140}$ of the vector y was determined. As a result, it was found that vectors corresponding to 23 resolving times, that is, the $2^{nd}$, $3^{rd}$, and $5^{th}$ to $25^{th}$ counted from the time of starting the measurement were not zero vectors and significant in value.

(a) in FIG. 6 is a drawing which shows internal image data when reconstruction is carried out by using only measurement data obtained at the 23 resolving times. Further, (b) in FIG. 6 is a drawing which shows internal image data, as a comparative example, when 23 resolving times are selected at random. As shown in (a) in FIG. 6 and (b) in FIG. 6, in the present example, it has been found that the 23 resolving times are appropriately selected to obtain a better image quality than that of the comparative example.

In the present example, in addition to the above results, under the condition that a reconstruction error is $\beta=1.00$, a vector y which met the conditional expression (28) was determined, and a vector which was not a zero vector among component vectors $y_1$ to $y_{140}$ of the vector y was determined. As a result, it has been found that vectors corresponding to 17 resolving times, that is, the $6^{th}$ to $22^{nd}$ counted from the time of starting the measurement are not zero vectors and significant in value.

(a) in FIG. 7 is a drawing which shows internal image data when reconstruction is carried out by using only measurement data obtained at the 17 resolving times. Further, (b) in FIG. 7 is a drawing which shows internal image data, as a comparative example, when 17 resolving times are selected at random. As shown in (a) in FIG. 7 and (b) in FIG. 7, in the present example, it has been found that the 17 resolving times are appropriately selected to obtain a better image quality than that of the comparative example.

In the present example, in addition, under the condition that a reconstruction error is $\beta=0.625$, a vector y which met the conditional expression (28) was determined, and a vector which is not a zero vector among component vectors $y_1$ to $y_{140}$ of the vector y was determined. As a result, vectors corresponding to 11 resolving times, that is, the $8^{th}$ to $18^{th}$ counted from the time of starting the measurement were not zero vectors and significant in value.

(a) in FIG. 8 is a drawing which shows internal image data when reconstruction is carried out by using only measurement data obtained at the 11 resolving times. Further, (b) in FIG. 8 is a drawing which shows internal image data, as a comparative example, when 11 resolving times are selected at random. As shown in (a) in FIG. 8 and (b) in FIG. 8, in the present example, it has been found that the 11 resolving times are appropriately selected to obtain a better image quality than that of the comparative example.

As apparent from the present example, in the measurement data selection method according to the above-described third modified example, measurement data are classified, for example, by the resolving times in time-resolved spectroscopy, thus making it possible to identify optimal resolving times among many resolving times. Then, only measurement data at the optimal resolving times are used to reconstruct internal image data, thus making it possible to obtain the internal image data excellent in image quality. In particular, according to the present example, it has been found that measurement data obtained at relatively early resolving times among the plurality of resolving times are effective in enhancing the image quality of the internal image data.

Figure 9:
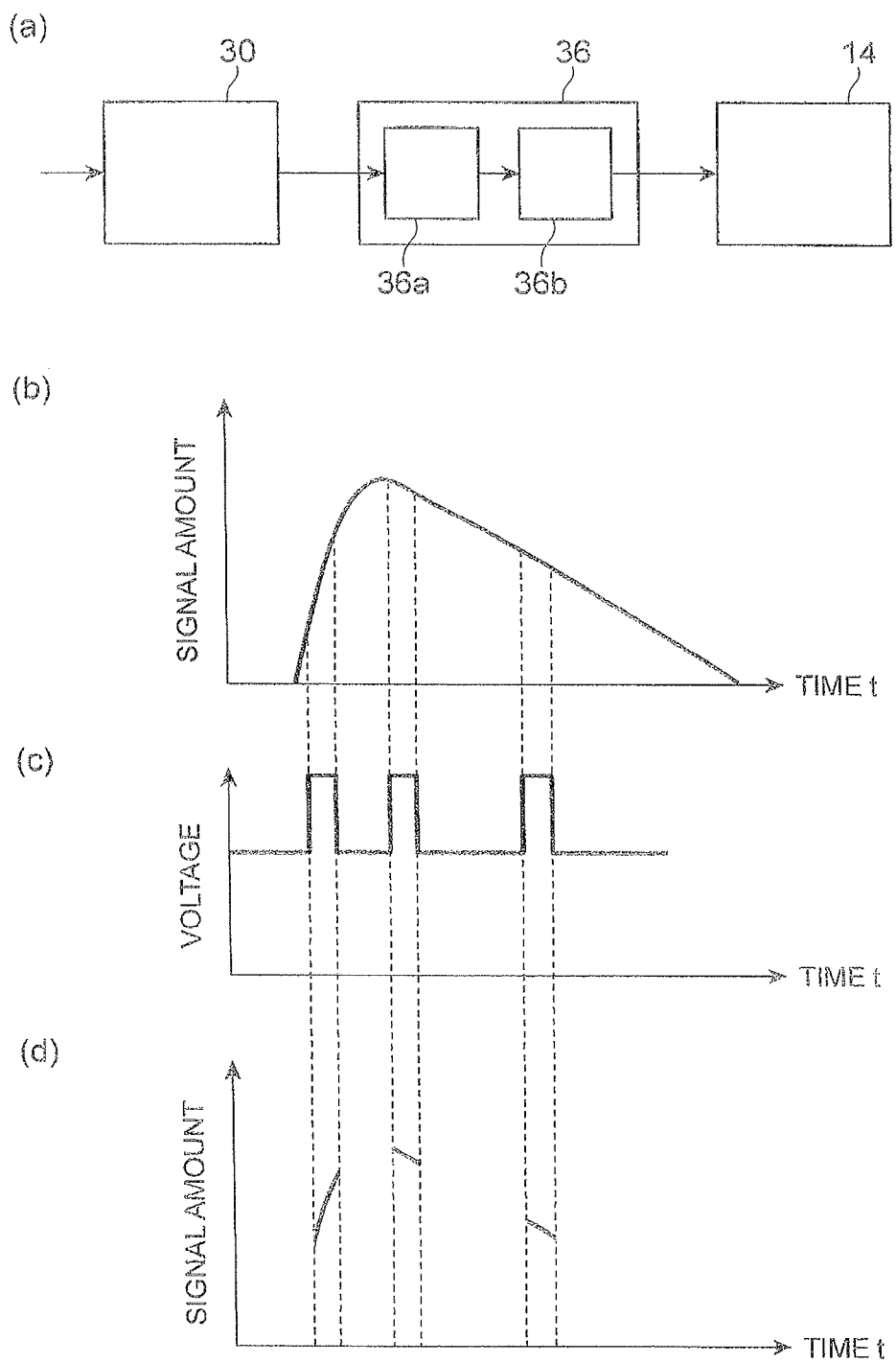
FIG. 9 (a) in FIG. 9 is a block diagram which shows a photodetector, a signal processing circuit, and a computing unit included in the bioinstrumentation apparatus. (b) in FIG. 9 shows an example of a detection signal waveform of scattered light obtained by the photodetector (typically, impulse response waveform). (c) in FIG. 9 shows an example of a gate signal waveform on a time gate circuit. (d) in FIG. 9 shows measurement data obtained at a data collecting unit.

Here, a description will be given of one example of a method in which the bioinstrumentation apparatus 10 is used to take out measurement data at any given resolving time. (a) in FIG. 9 is a block diagram which shows a photodetector 30, a signal processing circuit 36, and a computing unit 14 included in the bioinstrumentation apparatus 10. In order to take out only the measurement data at any given resolving time in the present example, as shown in the drawing given above, the signal processing circuit 36 is preferably provided with a time gate circuit (Time Gate Circuit; TGC) 36a and a data collecting unit 36b. In addition, (b) in FIG. 9 shows an example of a detection signal waveform of scattered light (typically, an impulse response waveform) obtained by the photodetector 30, (c) in FIG. 9 shows an example of a gate signal waveform in the time gate circuit 36a, and (d) in FIG. 9 shows measurement data obtained at the data collecting unit 36b. The bioinstrumentation apparatus 10 is constituted as described above, thus making it possible to implement favorably the measurement data selection method according to the present example.

Second Example

A description will be given of an example where classification is made according to a light emitting position in the above-described third modified example. In the present example, the measurement data selection method according to the third modified example is used to determine an optimal light emitting position.

Figure 10:
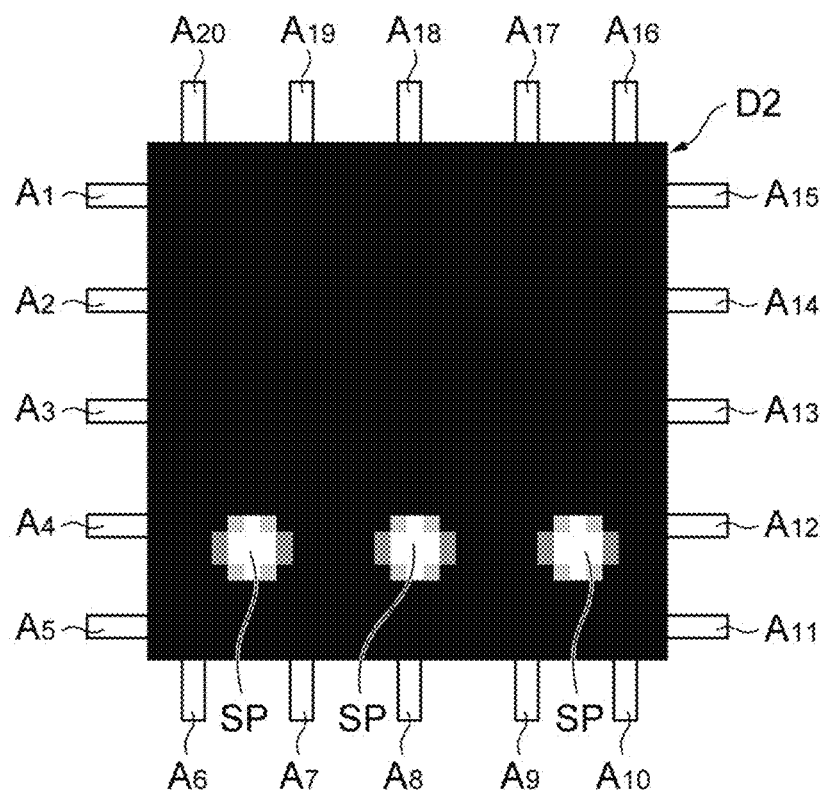
FIG. 10 is a drawing which shows learning image data used in a second example.

FIG. 10 is a drawing which shows learning image data D2 used in the present example, and the data includes a plurality of spots SP representing a tumor or the like. In addition, FIG. 10 also shows positions $A_1$ to $A_{20}$ of the light emitting/measurement ends 16 (that is, light emitting positions and light detection positions). In the present example, the measurement condition was set as follows.

Image size: 32×32
The number of light emitting positions: m=20
The number of light detection positions: m=20
Measurement time: 10 nano seconds
The number of resolving times (the number of time samplings): 50
Total number of measurement data: 20000

Then, the measurement was carried out under the above conditions to obtain 20000 pieces of measurement data. The measurement data were classified by the light emitting positions to give vectors $y_1$ to $y_{20}$, thereby defining the following vector y composed of the vectors $y_1$ to $y_{20}$.

[Formula 30]

$$y = \begin{pmatrix} y_1 \\ y_2 \\ \vdots \\ y_{20} \end{pmatrix} \quad (30)$$

Figure 11:
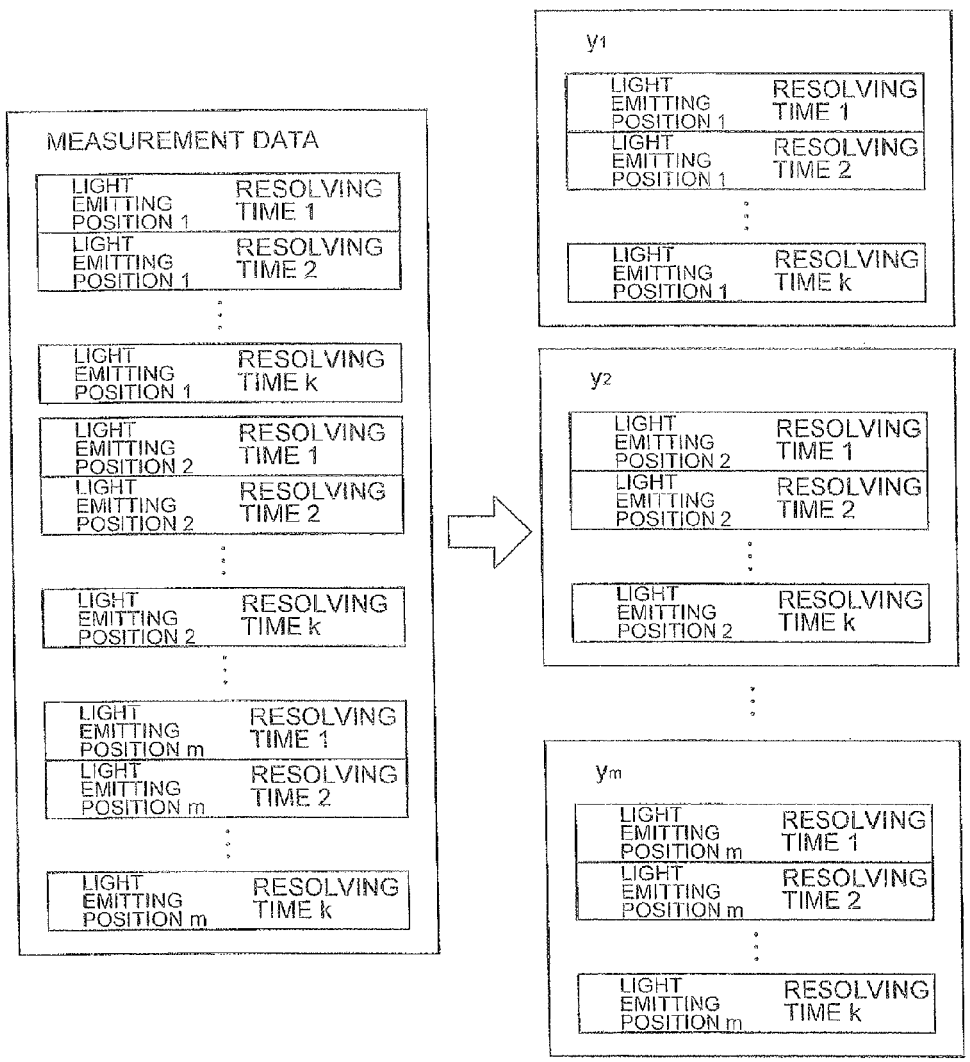
FIG. 11 is a drawing which conceptually shows an operation in which a plurality of measurement data are classified by the light emitting positions to give vectors $y_1$ to $y_m$.

In addition, FIG. 11 is a drawing which conceptually shows an operation in which a plurality of measurement data are classified by the light emitting positions to give vectors $y_1$ to $y_m$.

Further, where classification is made according to a light emitting position, the above-described conditional expression (28) may be modified as follows.

[Formula 31]

$$\min(\|y\|^0_0 + \beta \|z - H^T y\|_2^2) \quad (31)$$

Figure 12:
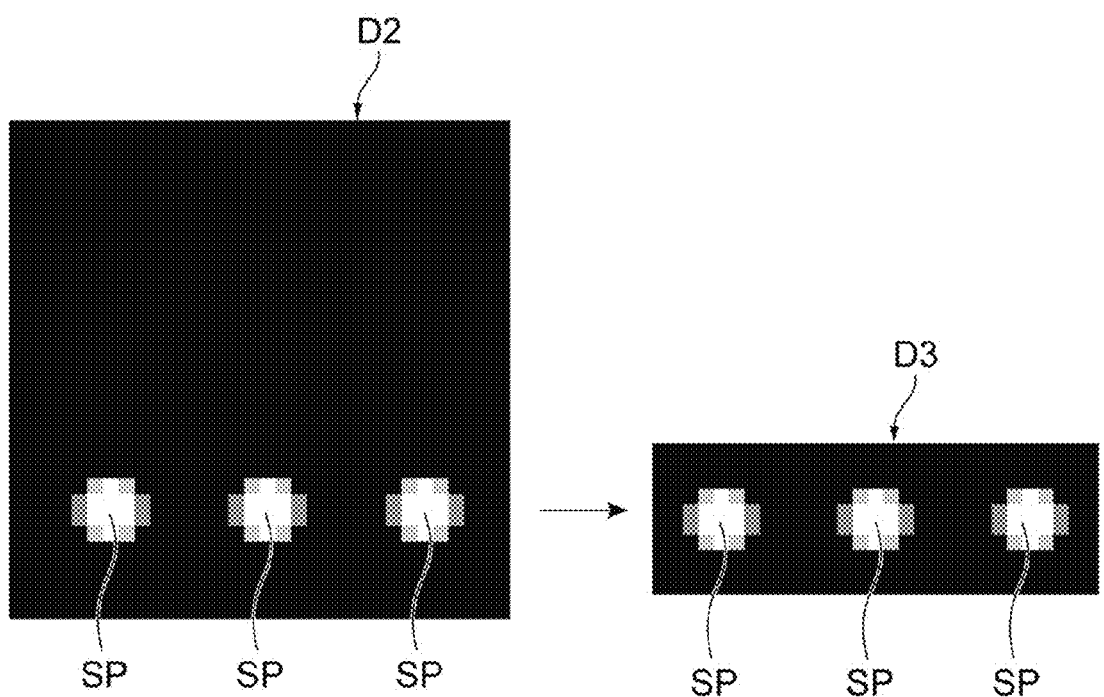
FIG. 12 is a drawing which shows a specific region of learning image data as an example.

Here, the vector z is a vector which shows pixel values of a specific region (a region in particular requiring an image quality, for example, a region at which a tumor is likely to develop) in the vector x showing respective pixel values of the learning image data D2. In addition, FIG. 12 is a drawing which shows a specific region D3 in the learning image data D2 as an example. Further, a system matrix H is a system matrix which has extracted a part relating to the vector z in the system matrix $A_2$.

Further, under the condition that a reconstruction error is $\beta$=0.5, a vector y which met the conditional expression (31) was determined, and a vector which was not a zero vector among component vectors $y_1$ to $y_{20}$ of the vector y was determined. As a result, as shown in (a) in FIG. 13, vectors corresponding to 9 light emitting positions close to the specific region D3 were not zero vectors and significant in value.

(a) in FIG. 14 is a drawing which shows internal image data when only measurement data corresponding to the 9 light emitting positions are used to carry out reconstruction. Further, (b) in FIG. 14 is a drawing which shows internal image data, as a comparative example, when the 9 light emitting positions are selected at random (more specifically, light emitting positions $A_2, A_3, A_5, A_8, A_{12}, A_{15}, A_{17}, A_{18}, A_{20}$). As shown in (a) in FIG. 14 and (b) in FIG. 14, in the present example, the 9 light emitting positions are selected appropriately, thus making it possible to obtain a better image quality than that of the comparative example.

In the present example, in addition to the above results, under the condition that a reconstruction error is $\beta$=0.3, a vector y which met the conditional expression (31) was determined, and a vector which was not a zero vector among component vectors $y_1$ to $y_{20}$ of the vector y was determined. As a result, as shown in (b) in FIG. 13, vectors corresponding to 3 light emitting positions close to the specific region D3 were not zero vectors and significant in value.

(a) in FIG. 15 is a drawing which shows internal image data when only measurement data corresponding to the 3 light emitting positions are used to carry out reconstruction. Further, (b) in FIG. 15 is a drawing which shows internal image data, as a comparative example, when the 3 light emitting positions are selected at random (more specifically, light emitting positions $A_{15}, A_{17}, A_{18}$). As shown in (a) in FIG. 15 and (b) in FIG. 15, in the present example, the 3 light emitting positions are selected appropriately, thus making it possible to obtain a better image quality than that of the comparative example.

In the present example, in addition, under the condition that a reconstruction error is $\beta$=0.25, a vector y which met the conditional expression (31) was determined, and a vector which was not a zero vector among component vectors $y_1$ to $y_{20}$ of the vector y was determined. As a result, as shown in (c) in FIG. 13, a vector corresponding to 1 light emitting position close to the specific region D3 was not a zero vector and significant in value.

(a) in FIG. 16 is a drawing which shows internal image data when only measurement data corresponding to the 1 light emitting position is used to carry out reconstruction. Further, (b) in FIG. 16 is a drawing which shows internal image data, as a comparative example, when the 1 light emitting position is selected at random (more specifically, the light emitting position $A_{15}$). As shown in (a) in FIG. 16 and in FIG. 16, in the present example, the 1 light emitting position is selected appropriately, thus making it possible to obtain a better image quality than that of the comparative example.

As apparent from the present example, in the measurement data selection method according to the above-described third modified example, it is possible to identify optimal light emitting positions for keeping an image quality among many light emitting positions, for example, by classifying measurement data by the light emitting positions. Then, only measurement data obtained at the optimal light emitting positions are used to reconstruct internal image data, thus making it possible to obtain internal image data excellent in image quality. In particular, a tumor such as cancer cells is likely to develop at a specific region at a high probability, and according to the present example, it has been found that measurement data corresponding to light emitting positions close to the specific region D3 among the plurality of light emitting positions are effective in enhancing the image quality of the internal image data.

In addition, where measurement data are classified by the light emitting positions as described in the present example, it is preferable that the bioinstrumentation apparatus 10 is additionally provided with light emitting position changeable means. The light emitting position changeable means is means which is constituted in such a manner that the light emitting/measurement ends 16 (refer to FIG. 1) for emitting measurement light are allowed to move to or allowed to be arranged selectively at 2 or more light emitting positions selected from a plurality of light emitting positions set in advance. For example, the light emitting position changeable means is constituted so as to irradiate measurement light from only the thus selected n (n is an integer of 1 or more, n<m) light emitting/measurement ends 16 among the m light emitting/measurement ends 16 which have been arranged in advance. The above-described light emitting position changeable means is favorably realized by supplying selectively measurement light, for example, only to the n light emitting/measurement ends 16 by the use of the optical switch 24. Alternatively, the light emitting position changeable means may control an actuator (not illustrated) installed on the light emitting/measurement ends 16 in such a manner that, for example, n light emitting/measurement ends 16 which have been provided in advance are allowed to move to n light emitting positions selected from m light emitting positions. Further, the light emitting position changeable means may be a mechanism which is constituted so that an operator is able to attach in a detachable manner, for example, n light emitting/measurement ends 16 to n light emitting positions selected from the m light emitting positions.

Figure 17:
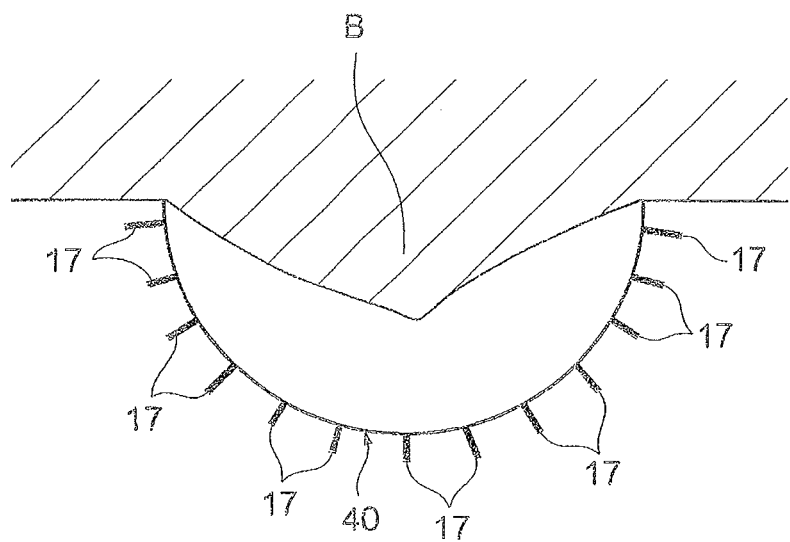
FIG. 17 is a drawing which shows one example of light emitting position changeable means.

FIG. 17 is a drawing which shows one example of the light emitting position changeable means. The light emitting position changeable means shown in the above drawing is provided with m folders 17 to which light emitting/measurement ends 16 can be attached in a detachable manner. The m folders 17 are installed on a measurement cup 40 with a predetermined interval. Here, the measurement cup 40 is a substantially semi-spherical container, with an upper end being opened, and as a measurement region B, for example, a breast is inserted into the measurement cup 40. Further, a liquid interface agent which is similar to the measurement region B in light absorption coefficient and light scattering coefficient is injected between the measurement region B and the measurement cup 40. (a) in FIG. 18 and (b) in FIG. 18 are drawings, each of which shows an example in which the light emitting/measurement ends 16 are disposed depending on a site at which a tumor E is present where the tumor E to be measured is present inside the measurement region B.

As described above, according to the light emitting position changeable means by which an operator is able to attach in a detachable manner the n light emitting/measurement ends 16 to the n light emitting positions selected from the m light emitting positions, it is possible to arrange a small number of light emitting/measurement ends 16 at optimal positions and prepare internal image data high in image quality. Here, in this case, it is preferable that the computing unit 14 of the bioinstrumentation apparatus 10 provides an operator with an optimal light emitting position through display means such as a display. Further, where there are no restrictions on the number of the light emitting/measurement ends 16, it is acceptable that the light emitting/measurement ends 16 are attached to all the folders 17 shown in the drawing and, among the thus obtained measurement data, only measurement data related to the above-described n light emitting/measurement ends 16 are used to prepare the internal image data.

Figure 19:
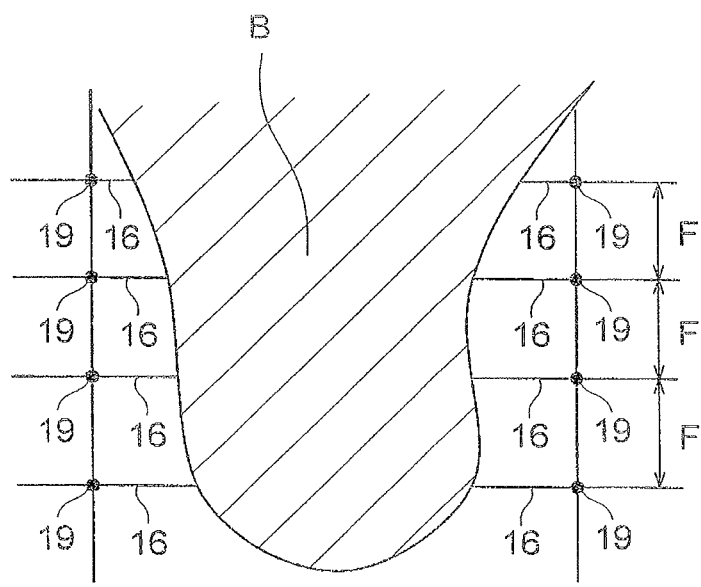
FIG. 19 is a drawing which shows another example of the light emitting position changeable means.

FIG. 19 is a drawing which shows another example of the light emitting position changeable means. The light emitting position changeable means shown in the above drawing is provided with a plurality of holder rings 19 to which the light emitting/measurement ends 16 are fixed. The plurality of holder rings 19 surround the measurement region B, and are arranged along a direction at which the measurement region B has been inserted. Further, an interval F between the plurality of holder rings 19 can be changed and actuated by an actuator (not illustrated) so that the light emitting/measurement ends 16 move to the n light emitting positions selected from the m light emitting positions. The light emitting/measurement end 16 comes into contact with the measurement region B and irradiates measurement light to the inside thereof.

The measurement data selection method for the bioinstrumentation apparatus, the light emitting position determination method for the bioinstrumentation apparatus, and the bioinstrumentation apparatus shall not be limited to the above-described embodiments but may be modified in various ways. For example, in the above-described embodiments, respective modified examples and respective examples, the computing unit of the bioinstrumentation apparatus computes conditional expressions to determine measurement data or a light emitting position to be selected, and further, the conditional expressions may be computed by a manufacturer when the bioinstrumentation apparatus is manufactured. In this case, it is preferable that the bioinstrumentation apparatus is completed in a state that the light emitting/measurement ends are arranged in advance at the selected optimal light emitting positions.

INDUSTRIAL APPLICABILITY

The present invention can be used as the measurement data selection method for the bioinstrumentation apparatus, the light emitting position determination method for the bioinstrumentation apparatus, and the bioinstrumentation apparatus which are capable of reducing the number of measurement data necessary for preparing image data to shorten the time for preparing the image data.

REFERENCE SIGNS LIST

10—bioinstrumentation apparatus, 14—computing unit, 16—light emitting/measurement end, 17—folder, 19—holder ring, 22—light source, 24—optical switch, 26—light source optical fiber, 28—emission optical fiber, 30—photodetector, 32—shutter, 34—detection optical fiber, 36—signal processing circuit, 36a—time gate circuit, 36b—data collecting unit, 38—displaying unit, 40—measurement cup, B—measurement region, D1, D2—learning image data, D3—specific region, P1—measurement light, P2—scattered light, SP—spot.

The invention claimed is:
1. A bioinstrumentation apparatus comprising:
a light emitting unit comprising a light source and optical switch for emitting pulse-shaped light to a measurement region of a subject from a plurality of light emitting positions that are connected to the optical switch by optical fiber; and
a computing unit comprising a processor and memory for preparing internal image data of the measurement region on the basis of a time-resolved waveform of diffused light from the measurement region obtained at a plurality of light detection positions, the bioinstrumentation apparatus, wherein
when a vector composed of measurement data $y_1$ to $y_{N1}$ (where N1 is an integer of 2 or more) obtained for respective combinations of the plurality of light emitting positions, the plurality of light detection positions, and a plurality of resolving times in the time-resolved waveform is given as

[Formula 11]

$$y = \begin{pmatrix} y_1 \\ y_2 \\ \vdots \\ y_{N1} \end{pmatrix}, \quad (1)$$

a vector in which pixel values of learning image data provided in advance as an example of the internal image data are components is given as x, and a system matrix for calculating the internal image data from the measurement data $y_1$ to $y_{N1}$ is given as $A_1$, the computing unit determines by inverse calculation the vector y which meets the following conditional expressions (2) and (3)

[Formula 12]

$$\min \|y\|_0^0 \quad (2)$$

[Formula 13]

$$\|x - A_1^T y\|_2^2 \leq \epsilon^2 \quad (3)$$

(where $\epsilon$ is any given constant number) or which meets the following conditional expression (4)

[Formula 14]

$$\min(\|y\|_0^0 + \beta \|x - A_1^T y\|_2^2) \quad (4)$$

(where $\beta$ is any given constant number), and upon measurement of the subject, prepares the internal image data by using only measurement data corresponding to components of the vector y which are not zero.

2. The bioinstrumentation apparatus according to claim 1, wherein the computing unit performs calculation by replacing an L0 norm of the vector y in the conditional expressions (2) and (4) with an L1 norm of the vector y.

3. The bioinstrumentation apparatus according to claim 1, wherein the computing unit performs calculation in such a manner that vectors in which pixel values of M pieces (M is an integer of 2 or more) of the learning image data provided in advance are components are given as $x_1$ to $x_M$, and

[Formula 15]

$$\|x - A_2^T y\|_2^2$$

in the conditional expressions (3) and (4) is replaced with

[Formula 16]

$$\sum_{i=1}^{M} \|x_i - A_1^T y\|_2^2.$$

4. The bioinstrumentation apparatus according to claim 1, wherein when the measurement data obtained for the respective combinations of the plurality of light emitting positions, the plurality of light detection positions, and the plurality of resolving times in the time-resolved waveform are classified into N2 (where N2 is an integer of 2 or more) groups according to a predetermined rule, a vector composed of vectors $y_1$ to $y_{N2}$ in which the measurement data for the respective N2 groups are components is given as

[Formula 17]

$$y = \begin{pmatrix} y_1 \\ y_2 \\ \vdots \\ y_{N2} \end{pmatrix}, \quad (5)$$

a vector in which pixel values of the learning image data provided in advance as an example of the internal image data are components is given as x, and a system matrix for calculating the internal image data from the vectors $y_1$ to $y_{N2}$ is given as $A_2$, the computing unit determines by inverse calculation, in place of the conditional expressions (2) to (4), the vector y which meets the following conditional expressions (6) and (7)

[Formula 18]

$$\min \sum_{j=1}^{N2} \|y_j\|_2^0 \left( \|y_j\|_2^0 = \lim_{\varepsilon \to +0} \|y_j\|_2^\varepsilon \right) \quad (6)$$

[Formula 19]

$$\|x - A_2^T y\|_2^2 \leq \varepsilon^2 \quad (7)$$

(where $\epsilon$ is any given constant number) or which meets the following conditional expression (8)

[Formula 20]

$$\min \left( \sum_{j=1}^{N2} \|y_j\|_2^0 + \beta \|x - A_2^T y\|_2^2 \right) \left( \|y_j\|_2^0 = \lim_{\varepsilon \to +0} \|y_j\|_2^\varepsilon \right) \quad (8)$$

(where $\beta$ is any given constant number), and upon measurement of the subject, prepares the internal image data by using only measurement data corresponding to components of the vector y which are not zero.

5. The bioinstrumentation apparatus according to claim 4, wherein the computing unit classifies the measurement data obtained for the respective combinations of the plurality of light emitting positions, the plurality of light detection positions, and the plurality of resolving times in the time-resolved waveform by the plurality of resolving times to give the vectors $y_1$ to $y_{N2}$.

6. The bioinstrumentation apparatus according to claim 4, wherein the computing unit classifies the measurement data obtained for the respective combinations of the plurality of light emitting positions, the plurality of light detection positions, and the plurality of resolving times in the time-resolved waveform by the plurality of light emitting positions to give the vectors $y_1$ to $y_{N2}$, and determines by inverse calculation the vector y which meets the conditional expressions (6) and (7) or the conditional expression (8), and the bioinstrumentation apparatus further comprises light emitting position changeable means which is constituted in such a manner that light emitting means for emitting the light is allowed to move to or allowed to be arranged selectively at the light emitting position corresponding to components of the vector y which are not zero.

\* \* \* \* \*